(12) United States Patent
Komatsu et al.

(10) Patent No.: US 10,208,470 B2
(45) Date of Patent: Feb. 19, 2019

(54) FLUSH TOILET, DEODORIZING DEVICE, AND DEODORIZING METHOD

(71) Applicant: LIXIL Corporation, Tokyo (JP)

(72) Inventors: Toshihiko Komatsu, Tokyo (JP); Hiroaki Watanabe, Tokyo (JP); Yasuyuki Furutani, Tokyo (JP); Dai Goto, Tokyo (JP); Takuma Uchiyama, Tokyo (JP); Kensaku Hiraoka, Tokyo (JP); Tomoya Sasaki, Tokyo (JP)

(73) Assignee: Lixil Corporation, Tokyo (JP)

( * ) Notice: Subject to any disclaimer, the term of this patent is extended or adjusted under 35 U.S.C. 154(b) by 0 days.

(21) Appl. No.: 15/295,069

(22) Filed: Oct. 17, 2016

(65) Prior Publication Data

US 2017/0067240 A1    Mar. 9, 2017

Related U.S. Application Data

(63) Continuation of application No. PCT/JP2015/059685, filed on Mar. 27, 2015.

(30) Foreign Application Priority Data

Apr. 18, 2014 (JP) ................... 2014-086359

(51) Int. Cl.
*E03D 9/052* (2006.01)
*E03D 9/00* (2006.01)
(Continued)

(52) U.S. Cl.
CPC ............... *E03D 9/052* (2013.01); *A61L 9/04* (2013.01); *A61L 9/122* (2013.01); *E03D 9/00* (2013.01); *E03D 9/05* (2013.01); *E03D 9/08* (2013.01)

(58) Field of Classification Search
USPC ............................................. 4/352, 210–221
See application file for complete search history.

(56) References Cited

U.S. PATENT DOCUMENTS 5,210,884 A    5/1993 Redford
5,454,122 A   10/1995 Bergeron
(Continued)

FOREIGN PATENT DOCUMENTS

CN           2804209 Y     8/2006
CN         201172870 Y    12/2008
(Continued)

OTHER PUBLICATIONS

International Search Report from International Application No. PCT/JP2015/059685 dated Jun. 9, 2015.
(Continued)

*Primary Examiner* — Lauren Crane
(74) *Attorney, Agent, or Firm* — Muncy, Geissler, Olds & Lowe, P.C.

(57) ABSTRACT

A method for removing odors produced in a toilet main unit of a toilet is made available. Specifically, a deodorizing unit having an air expulsion port and an air suctioning port is provided in a rear portion of the toilet main unit, and air is circulated by expelling air through the expulsion port such as to laterally swirl the air along an inner surface of the toilet's bowl, and by suctioning swirled returning air via the suctioning port. Deodorization is carried out in the course of circulating the air.

7 Claims, 14 Drawing Sheets

(51) Int. Cl.
*E03D 9/05* (2006.01)
*A61L 9/04* (2006.01)
*A61L 9/12* (2006.01)
*E03D 9/08* (2006.01)

(56) References Cited

U.S. PATENT DOCUMENTS 6,457,186 B1 10/2002 Stewart
2008/0256692 A1* 10/2008 Barton .................. A47K 13/307
4/213

FOREIGN PATENT DOCUMENTS

| | | |
|---|---|---|
| JP | S59-177399 U | 11/1984 |
| JP | H05-346034 A | 12/1993 |
| JP | H0827861 A | 1/1996 |
| JP | H11-181867 A | 7/1999 |
| JP | 2003213764 A | 7/2003 |
| JP | 2008-095440 A | 4/2008 |
| JP | 2008-297785 A | 12/2008 |
| KR | 20100107642 A | 10/2010 |

OTHER PUBLICATIONS

Search Report dated Dec. 28, 2017 in corresponding CN Application No. 2015800202896 and English translation thereof, pp. 1-4.
Yu et al., "Talking About Household Appliance and Health," Jan. 31, 2001, 4 pages.

* cited by examiner

FLUSH TOILET, DEODORIZING DEVICE, AND DEODORIZING METHOD

BACKGROUND OF THE INVENTION

1. Field of the Invention

The present invention relates to flush toilets, and in particular relates to a deodorizing method for removing odors produced in a toilet main unit.

2. Description of the Related Art

Some flush toilets are provided with a deodorizing device that absorbs and removes the odors of toilet usage. Accompanying the switchover to low-silhouette toilets, deodorizing devices of this kind are often furnished on the upper side of the rear portion of the toilet fixture as a unit integrated with a device for pubic lavage (c.f. Patent Document 1, for example). Deodorizing devices of this type, having a suction port opening toward the toilet bowl, suction in and remove odors from stale air over the toilet bowl, which is then discharged exteriorly.

Patent Document 1 Japanese Unexamined Pat. App. Pub. No. 2008-297785

Owing to restrictions on the size of the suction port in the deodorizing device, however, thoroughly suctioning out the stale air over the toilet bowl has meant that the output power of the fan must be enlarged, wherein from an efficiency perspective there has been room for improvement.

SUMMARY OF THE INVENTION

One object of the present invention, brought about taking such issues into consideration, is to make available a method for enabling efficient removal of odors produced in a flush toilet.

To solve the problem above, one embodiment of the present invention is a deodorizing method for removing odors within a flush-toilet toilet bowl. The deodorizing method comprises: providing, in a rear portion of a toilet main unit, a deodorizing device having an air expulsion port and an air suctioning port; circulating air by expelling air through the expulsion port such as to laterally swirl the air along an inner surface of the toilet bowl, and suctioning swirled returning air via the suctioning port; and carrying out deodorization in the course of circulating the air.

Another embodiment of the present invention is a deodorizing device. The deodorizing device for removing odors within a flush-toilet toilet bowl, comprises: a deodorization passage, provided in a rear portion of a toilet main unit, having at one end thereof an air expulsion port, having at another end thereof an air suctioning port, and furnished midway thereof with a deodorizing section; and a blower enabled for generating a flow of air in the deodorization passage; wherein the expulsion port is arranged so as to open in a direction enabling air expelled therefrom to swirl laterally along an inner surface of the toilet bowl, and the suctioning port is arranged so as to open on a flow pathway of air returning from swirling along the toilet bowl.

Yet another embodiment of the present invention is a flush toilet. The flush toilet is furnished with a deodorizing device for removing odors within a main unit of the toilet, and the deodorizing device comprises: a deodorization passage, provided in a rear portion of the toilet main unit, having at one end thereof an air expulsion port, having at another end thereof an air suctioning port, and furnished midway thereof with a deodorizing section; and a blower enabled for generating a flow of air in the deodorization passage; wherein the expulsion port is arranged so as to open in a direction enabling air expelled therefrom to swirl laterally along an inner surface of a bowl of the toilet, and the suctioning port is arranged so as to open on a flow pathway of air returning from swirling along the toilet bowl, the flush toilet is configured to enable an air-swirling passage within the toilet bowl, and said deodorization passage to form a circulation passage for circulating air, and the swirling passage is configured by a rim-like pathway formed in an upper portion of the toilet main unit.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

In the following, an embodiment of the present invention will be described in detail with reference to the drawings. In the following description, front and rear positions in the toilet structure may be expressed based on positional relationships viewed from a user of the toilet sitting on the seat, for the sake of convenience.

Figure 1:
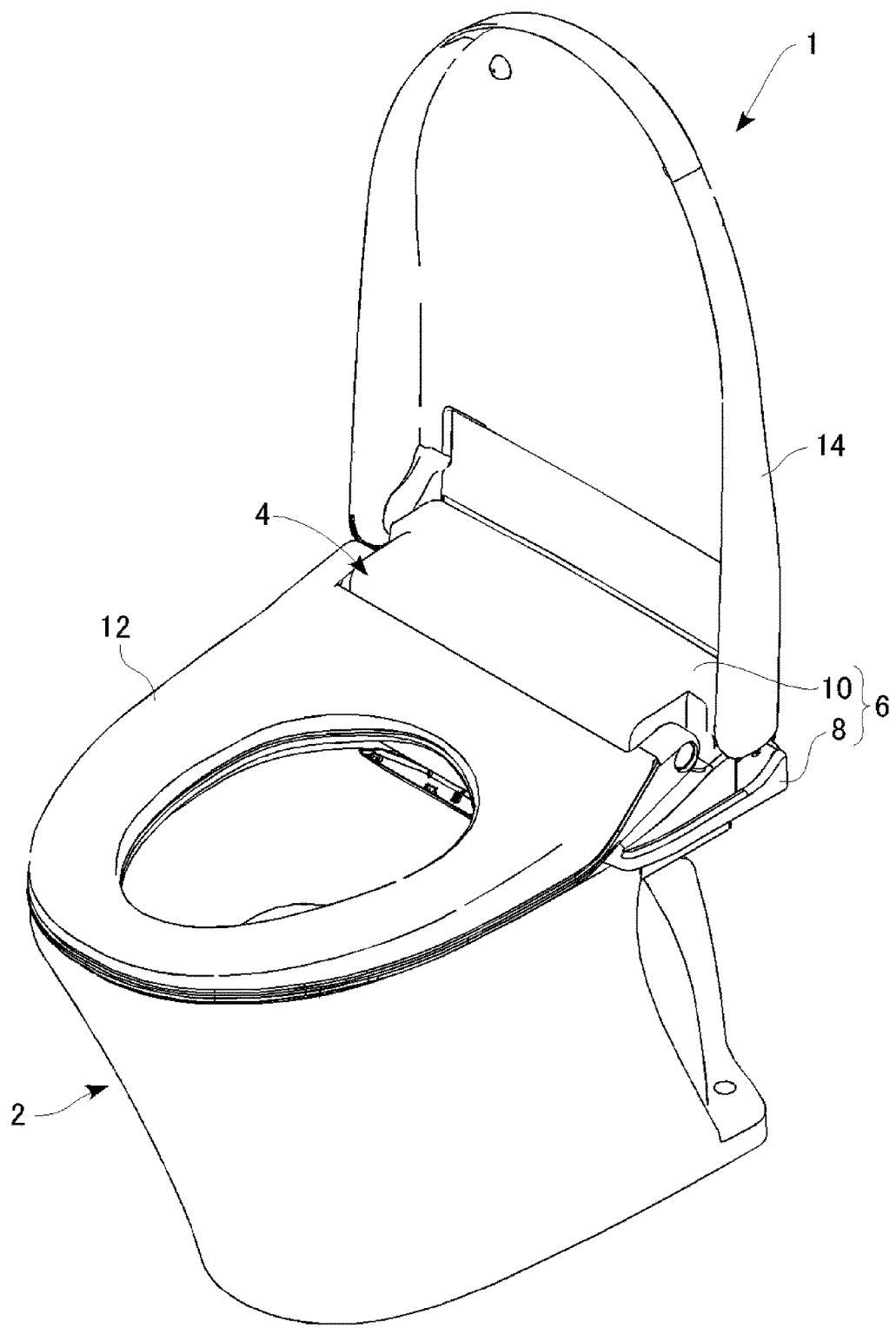
FIG. 1 is a perspective view of a toilet provided with a private part washing device according to an embodiment, viewed obliquely from an upper front side.
Figure 2:
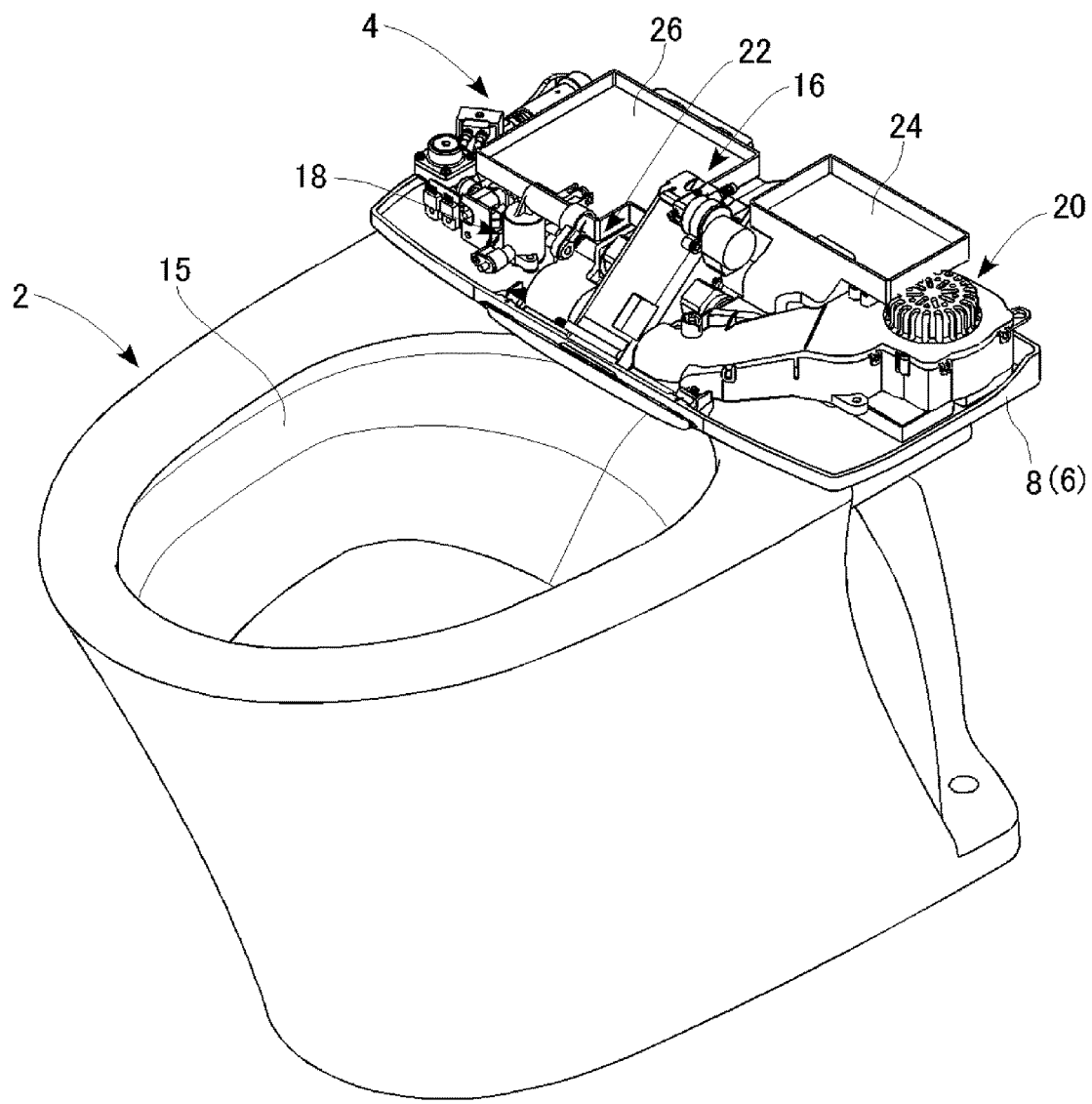
FIG. 2 is a perspective view of the toilet shown in FIG. 1 and shows the state where the toilet lid, the toilet seat, and the cover of the private part washing device have been removed.

FIG. 1 is a perspective view of a toilet provided with a private part washing device according to an embodiment, viewed obliquely from an upper front side. FIG. 2 is a perspective view of the toilet shown in FIG. 1 and shows the state where the toilet lid, the toilet seat, and the cover of the private part washing device have been removed.

As shown in FIG. 1, a toilet 1 is a flush toilet and comprises a private part washing device 4 on a rear portion of a toilet main unit 2. The private part washing device 4 has a case 6 that houses various functional components used for private part washing and warm air drying. The case 6 includes a base 8 provided on the upper surface of the rear portion of the toilet main unit 2 and a cover 10 fitted to the base 8. To the cover 10, a toilet seat 12 and a toilet lid 14 are rotatably attached. Although the toilet 1 is also provided with a tank for storing flush water, various functional components including a pump for supplying flush water and valves, pipes, and the likes, the description thereof will be omitted.

The toilet main unit 2 comprises a toilet bowl 15 for receiving waste, as shown in FIG. 2, and also comprises a drain pipe section, not illustrated, that extends downward from the bottom of the toilet bowl 15. Although not shown in the figure, in the upper portion of the toilet bowl 15, a rim water passage for generating a swirling flow of flush water along the periphery thereof, and a drop-in passage for generating a flow to drop the swirling flow into the drain pipe section are formed.

The private part washing device 4 comprises a nozzle unit 16 including a pair of private part washing nozzles, a warm water supply unit 18 for supplying warm water to the nozzle unit 16, a warm air drying unit 20 driven for warm air drying, a deodorizing unit 22 for removing odors produced in the toilet main unit 2, a control substrate 24 for controlling driving of each unit, and a power supply substrate 26 for supplying power to the control substrate 24 and various functional components.

Figure 3A:
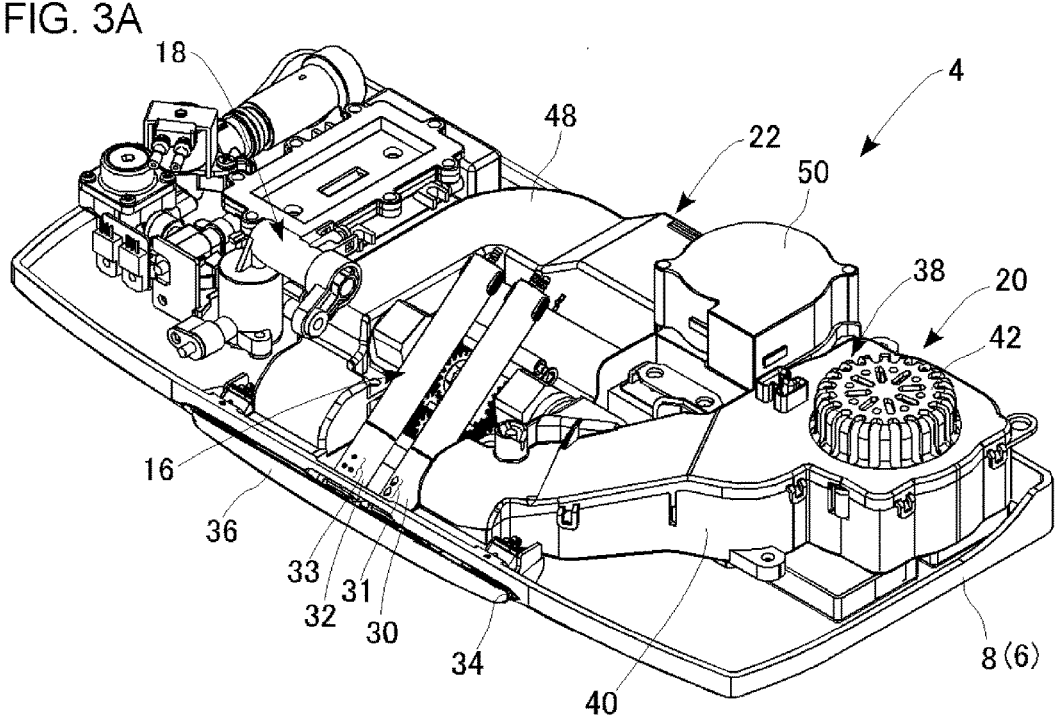
FIGS. 3A-3B are diagrams that each show an internal structure of the private part washing device.
Figure 3B:
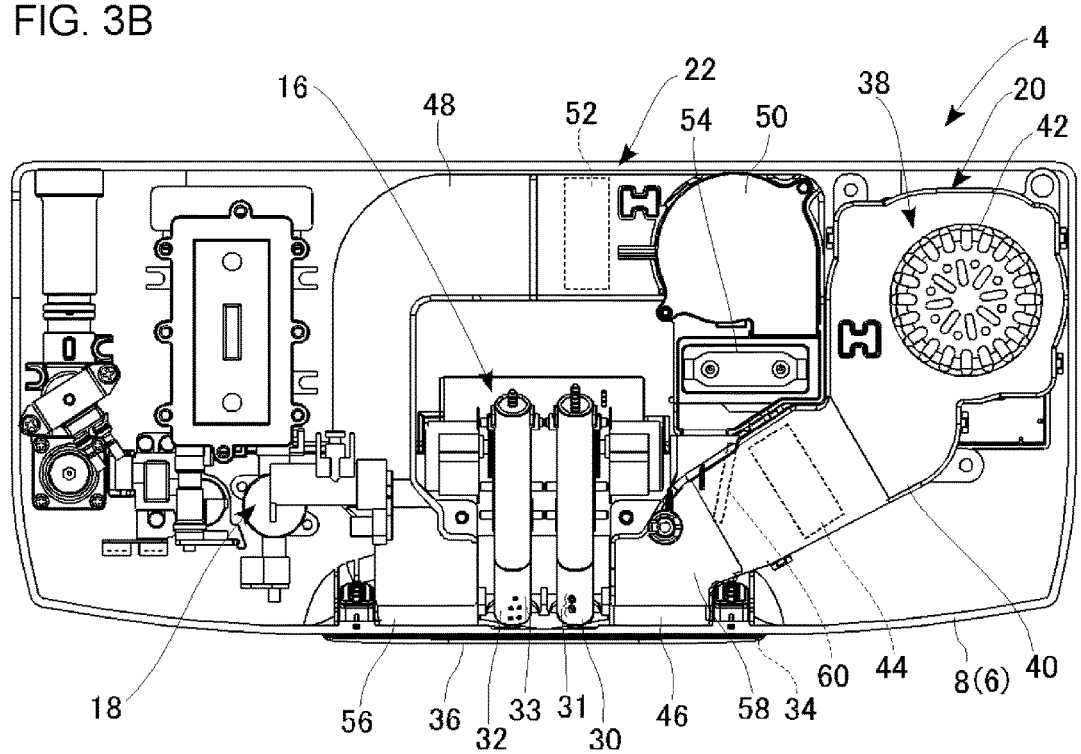
Figure 4A:
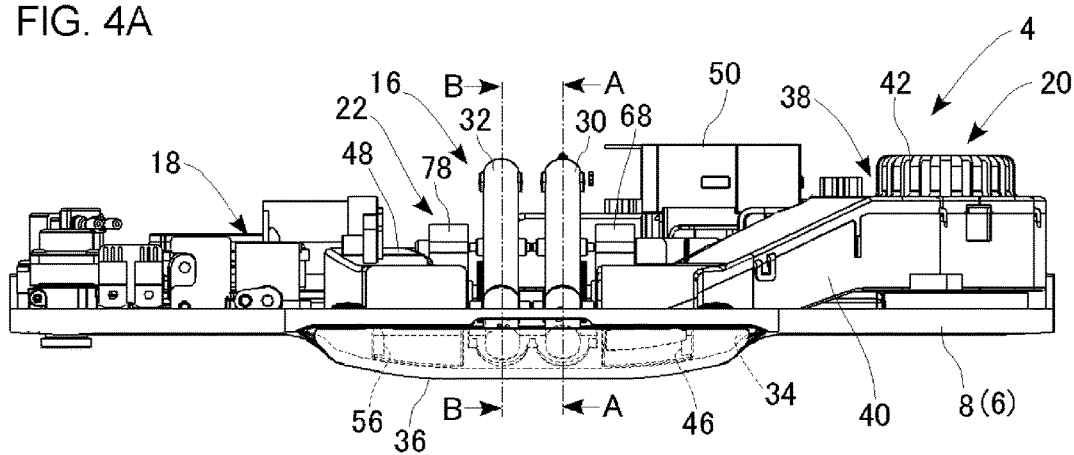
FIGS. 4A-4C are diagrams that each show an internal structure of the private part washing device.
Figure 4B:
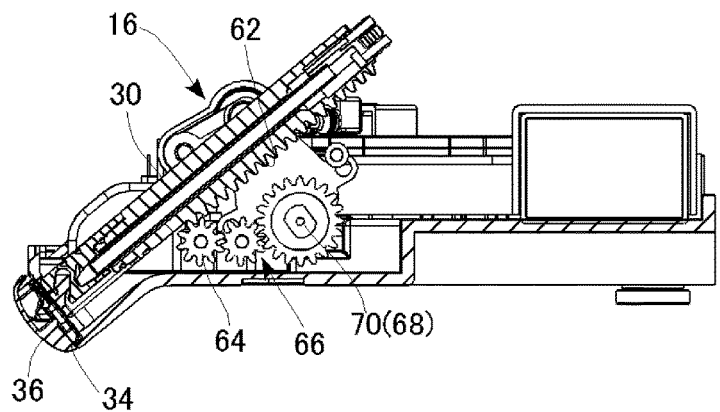
Figure 4C:
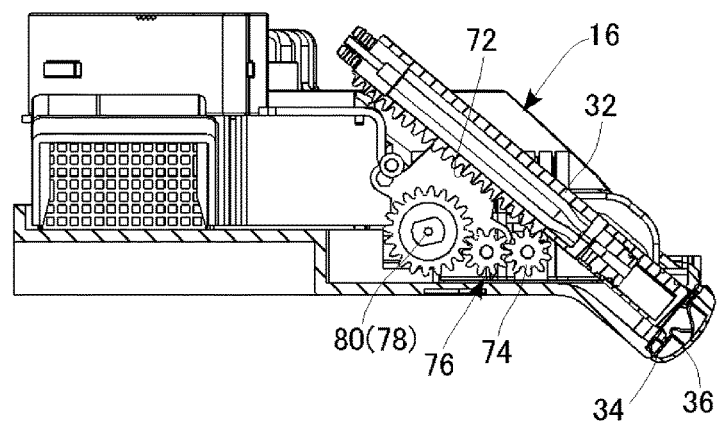

FIGS. 3A-3B and 4A-4C are diagrams that each show an internal structure of the private part washing device 4. FIG. 3A is a perspective view, and FIG. 3B is a plan view. FIG. 4A is a front view. FIG. 4B is a sectional view taken along line A-A of FIG. 4A viewed from the arrow direction, and FIG. 4C is a sectional view taken along line B-B of FIG. 4A viewed from the arrow direction. Each of the figures shows the state where the cover 10 of the private part washing device 4, the cover of the nozzle unit 16, the control substrate 24, and the power supply substrate 26 have been removed, for the sake of convenience.

As shown in FIGS. 3A and 3B, the nozzle unit 16 is arranged in a center part of the base 8. The nozzle unit 16 comprises washing nozzles 30 and 32 arranged side by side as a pair of private part washing nozzles (twin nozzles). The washing nozzle 30 is an anus washing nozzle and functions as a "first washing nozzle". The washing nozzle 32 is a bidet nozzle and functions as a "second washing nozzle". The washing nozzles 30 and 32 are supported by a supporting structure provided on the base 8 so that the nozzles are tilted downward toward the front side and in parallel with each other. The washing nozzles 30 and 32 have spray holes 31 and 33, respectively, from which washing water is sprayed, at the lower end parts. On a center part of the front of the base 8 (case 6), an opening 34 of a rectangular shape is provided, and the washing nozzles 30 and 32 can protrude forward through the opening 34. Further, a shutter 36 used to open and close the opening 34 is also provided on the front side of the base 8, and the structure and operation thereof will be described later in detail.

The warm water supply unit 18 is arranged in a space on the right side of the base 8 and connected to the washing nozzles 30 and 32 via the respective pipes. The warm water supply unit 18 supplies, to the washing nozzles 30 and 32, warm water adjusted to a preset temperature, according to an instruction from the control substrate 24.

The warm air drying unit 20 is arranged in a space on the left side of the base 8. The warm air drying unit 20 includes a warm airflow generator 38 and a warm air duct 40. The warm airflow generator 38 includes a fan (blower) 42 placed on the upstream side of the warm air duct 40, and a heater 44 placed midway along the warm air duct 40. The upstream end of the warm air duct 40 functions as an air inlet, not illustrated, and is opened to the atmosphere. The downstream end of the warm air duct 40 functions as an expulsion port 46 of warm air and is provided on the opening 34 (see FIG. 4A). By driving the fan 42, outside air is introduced into the warm air duct 40 and warmed by the heater 44. The warmed air that has passed through the heater 44 then blows out forward from the expulsion port 46.

The deodorizing unit 22 is arranged in a center part of the base 8 so as to surround the nozzle unit 16. The deodorizing unit 22 includes a deodorization duct 48 arranged so as to surround the nozzle unit 16, a fan (blower) 50 placed midway along the deodorization duct 48, a deodorizing cartridge 52 placed on the upstream side of the fan 50, and a bacteria removal unit 54 placed on the downstream side of the fan 50.

The deodorizing cartridge 52 contains a deodorizing catalyst and functions as a "deodorizing section" for removing odors included in passing air. Although an absorption type deodorizer, having activated carbon or the like as a catalyst, is employed in the present embodiment, a decomposition type deodorizer, having a photocatalyst with the function to decompose a substance by irradiation of ultraviolet rays or other light rays, for example, may also be employed. The bacteria removal unit 54 generates sterilization ions to prevent propagation of floating bacteria or remove bacteria. More specifically, the bacteria removal unit 54 ionizes air to generate positive ions and negative ions, with which floating bacteria are surrounded so as to be inactivated.

The deodorization duct 48 functions as a "deodorization passage". The upstream end of the deodorization duct 48 functions as a suction port 56 for odorous air and is provided on the opening 34 (see FIG. 4A). The downstream end of the deodorization duct 48 is connected to the downstream side of the heater 44 in the warm air duct 40.

Namely, the downstream end of the warm air duct 40 is used as a shared passage 58 of the deodorization passage and the warm airflow passage. Accordingly, the expulsion port 46 of the warm air duct 40 is also used as the expulsion port of the deodorization duct 48. At the upstream end of the shared passage 58, i.e., the connecting part of the deodorization duct 48 and warm air duct 40, a damper 60 is provided to switch the passages and adjust the air volume. With an adjusted angle of the damper 60, the ratio between the opening of the warm air duct 40 and the opening of the deodorization duct 48 can be controlled.

As shown in FIGS. 4A and 4B, the washing nozzle 30 has a cylindrical shape and is driven in the axial directions by a rack and pinion mechanism. On the lower surface of the washing nozzle 30, a rack 62 is formed to mesh with a pinion 64. The pinion 64 is connected to a rotating shaft 70 of a motor 68 via a gear mechanism 66. With such a configuration, by rotating the motor 68 in one direction, the washing nozzle 30 can be moved downward in the axial direction so as to protrude forward through the opening 34. Also, by rotating the motor 68 in the other direction in this state, the washing nozzle 30 can be moved upward in the axial direction so as to recede from the opening 34. The motor 68 and the rack and pinion mechanism constitute a "nozzle drive unit". In the present embodiment, by driving the washing nozzle 30 downward, the shutter 36 can be pushed and rotated to be opened.

As shown in FIGS. 4A and 4C, the washing nozzle 32 also has a cylindrical shape and is driven in the axial directions by a rack and pinion mechanism. On the lower surface of the washing nozzle 32, a rack 72 is formed to mesh with a pinion 74. The pinion 74 is connected to a rotating shaft 80 of a motor 78 via a gear mechanism 76. With such a configuration, by rotating the motor 78 in one direction, the washing nozzle 32 can be moved downward in the axial direction so as to protrude forward through the opening 34. Also, by rotating the motor 78 in the other direction in this state, the washing nozzle 32 can be moved upward in the axial direction so as to recede from the opening 34. The motor 78 and the rack and pinion mechanism constitute a "nozzle drive unit". In the present embodiment, by driving the washing nozzle 32 downward, the shutter 36 can be pushed and rotated to be opened.

Figure 5A:
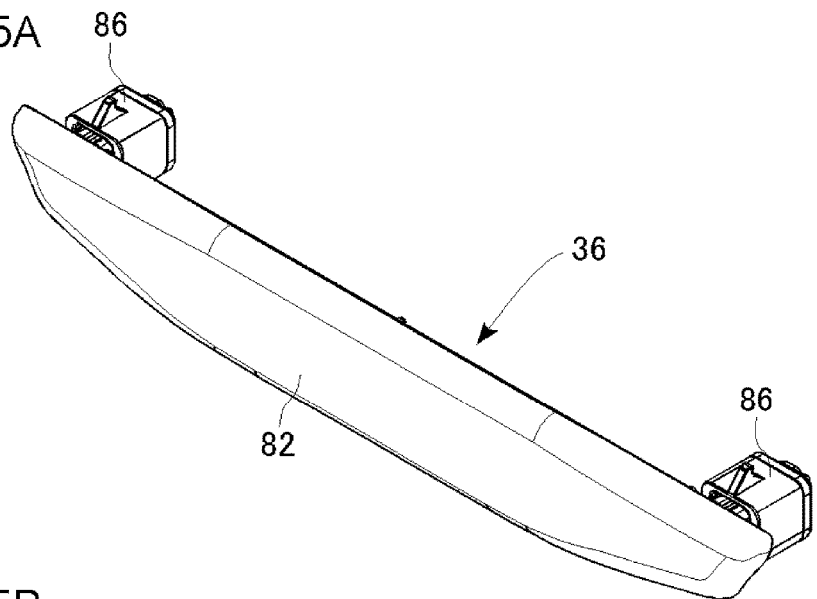
FIGS. 5A-5C are diagrams that each show a configuration of a shutter.
Figure 5B:
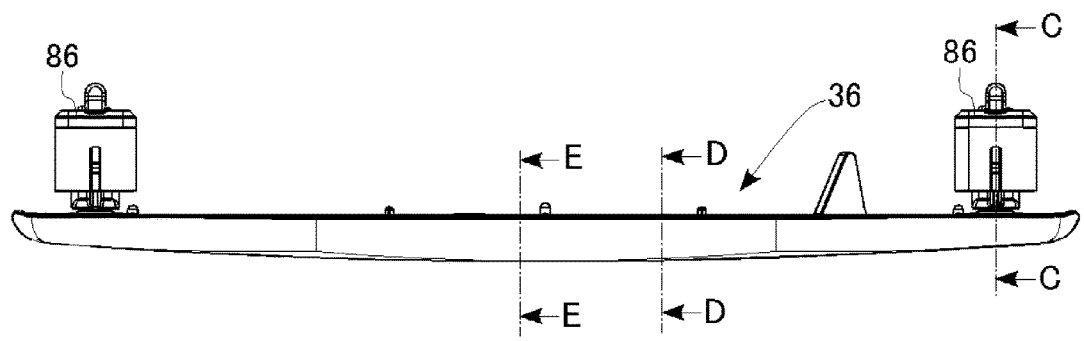
Figure 5C:
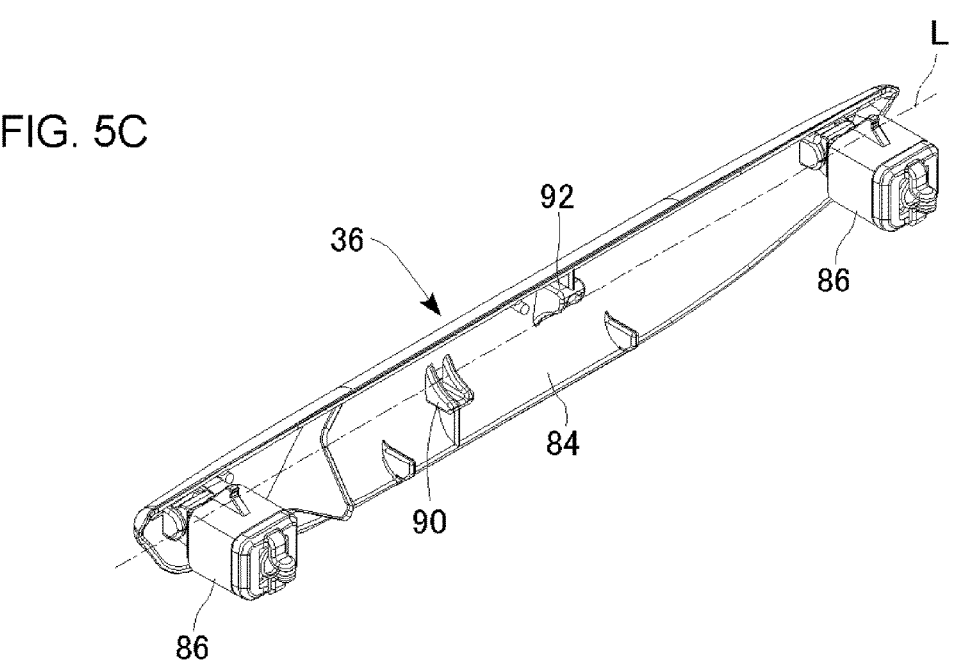
Figure 6A:
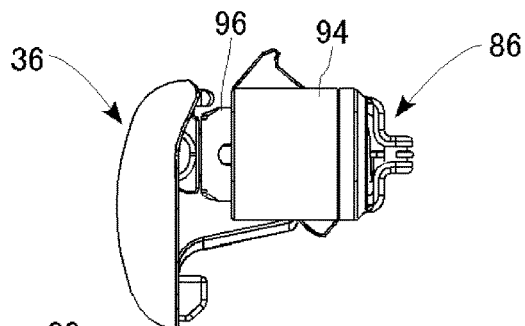
FIGS. 6A-6E are diagrams that each show a configuration of the shutter.
Figure 6B:
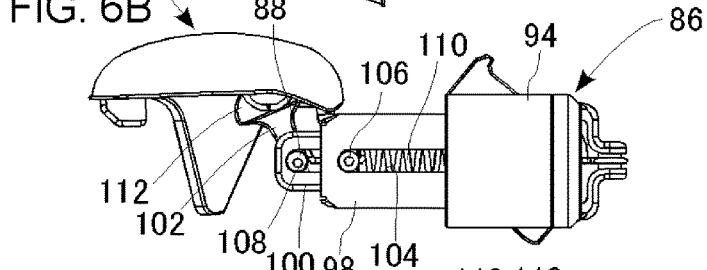
Figure 6C:
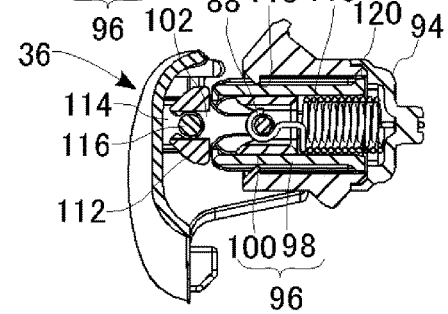
Figure 6D:
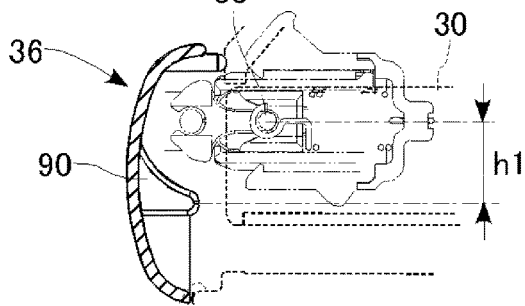
Figure 6E:
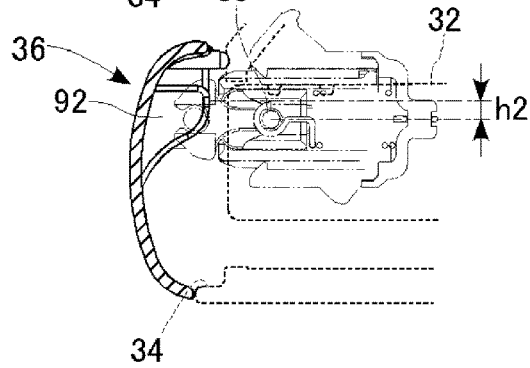

FIGS. 5A-5C and 6A-6E are diagrams that each show a configuration of the shutter 36. FIG. 5A is a perspective view viewed obliquely from a front side, FIG. 5B is a plan view, and FIG. 5C is a perspective view viewed obliquely from a rear side. FIG. 6A is a side view that shows a closing state, FIG. 6B is a side view that shows an upward opening state, and FIG. 6C is a view taken along line C-C of FIG. 5B viewed from the arrow direction. FIG. 6D is a view taken along line D-D of FIG. 5B viewed from the arrow direction. FIG. 6E is a view taken along line E-E of FIG. 5B viewed from the arrow direction.

As shown in FIGS. 5A-5C, the shutter 36 has an almost rectangular shape, and a center part thereof in a vertical direction slightly bulges forward to form a curved surface. In the closing state shown in the figures, the front of the shutter 36 is an outer surface 82 exposed to the toilet bowl 15 side, and the rear thereof is an inner surface 84 facing the inside of the device (the inside of the case 6). To the inner surface 84, a pair of rotational support mechanisms 86 are detachably fitted. The rotational support mechanisms 86 are also detachably fitted into a pair of mounting holes provided in the opening 34 of the case 6. Each of the pair of rotational support mechanisms 86 has a rotational shaft 88 (see FIG. 6), which will be described later, for rotatably supporting the both ends of the shutter 36. The rotational support mechanisms 86 will be detailed later.

As shown in FIG. 5C, on a center part of the inner surface 84 of the shutter 36, engaging protrusions 90 and 92 are provided with a space therebetween in a width direction. The engaging protrusion 90 functions as a "first engagement part", and the engaging protrusion 92 functions as a "second engagement part". The engaging protrusions 90 and 92 are provided at positions facing the washing nozzles 30 and 32, respectively. However, the shapes of the engaging protrusions 90 and 92 protruding from the inner surface 84 are different so that the shutter 36 can be upwardly or downwardly opened in cooperation with the respective washing nozzles.

More specifically, the shape of the engaging protrusion 90 is determined so that the tip thereof is positioned lower than the axial line L of the rotational shaft 88 in the closing state of the shutter 36. Also, the shape of the engaging protrusion 92 is determined so that the tip thereof is positioned higher than the axial line L of the rotational shaft 88 in the closing state of the shutter 36. With such configurations, when the washing nozzle 30 pushes the engaging protrusion 90 forward, the force acts to push forward a position lower than the rotational shaft 88 on the shutter 36, so that the shutter 36 can be upwardly opened. Also, when the washing nozzle 32 pushes the engaging protrusion 92 forward, the force acts to push forward a position higher than the rotational shaft 88 on the shutter 36, so that the shutter 36 can be downwardly opened.

In the present embodiment, the configurations of the nozzle drive units, rotational support mechanisms 86, and shutter 36 set forth above function as a "shutter switching mechanism" for switching the state of the shutter 36 among the closing state, upward opening state, and downward opening state. The configurations and operations for enabling the upward opening and downward opening will be detailed later.

As shown in FIGS. 6A-6C, each of the rotational support mechanisms 86 is configured by fitting a slide arm 96 to a case 94 of a bottomed cylindrical shape so that the slide arm 96 is partially inserted into the case 94. The slide arm 96 has a double structure in which an outer cylinder 98 and an inner cylinder 100 are concentrically fitted. The outer cylinder 98 is slidably supported by the case 94, and the inner cylinder 100 is slidably supported by the outer cylinder 98. To the inner cylinder 100, a shutter arm 102 is rotatably fitted.

On each side wall of the outer cylinder 98, a slit 104 having a predetermined length extending in an axial direction is formed, and a guide shaft 106 is inserted through the slits 104 so as to protrude through the both side walls of the inner cylinder 100. Accordingly, the inner cylinder 100 can be displaced relative to the outer cylinder 98 within the movable range of the guide shaft 106 along the slits 104. Also, on each side wall of the inner cylinder 100 is formed a slit 108 having a predetermined length extending in an axial direction, and the rotational shaft 88, provided at the base end part of the shutter arm 102, is inserted through the slits 108. Accordingly, the shutter arm 102 can be displaced relative to the inner cylinder 100 within the movable range of the rotational shaft 88 along the slits 108. Therefore, the rotational shaft 88 is a rotation support as the center of rotation of the shutter 36 and is also a movable support (movable shaft) that can be moved in the front-back directions of the shutter 36.

As shown in FIG. 6C, between the bottom of the case 94 and the inner cylinder 100, a spring 110 is placed to bias the inner cylinder 100 in the pulling direction. One end of the spring 110 is fixed to the bottom of the case 94, and the other end thereof is fixed to the rotational shaft 88. At the tip of the shutter arm 102, a click portion 112 for fitting is provided. Also, at a position on the inner surface 84 of the shutter 36 facing the shutter arm 102, a protrusion 114 for fitting is provided. The tip of the protrusion 114 is formed as a shaft portion 116 extending in a horizontal direction, and the click portion 112 is detachably connected to the shaft portion 116 so as to pinch the shaft portion 116. The click portion 112 functions as a "chuck mechanism" that holds a part of the shutter 36. When the shutter arm 102 is connected to the shutter 36, the rotational shaft 88 and the shaft portion 116 are positioned on the same horizontal plane, as shown in FIG. 6C. When the rotational support mechanisms 86 are attached to the case 6, the pair of rotational shafts 88 extend in a horizontal direction to rotatably support the shutter 36.

As shown in FIG. 6C, since the width of the click portion 112 is greater than the width of the opening of the outer cylinder 98, the click portion 112 cannot enter the outer cylinder 98 and is caught at the opening end of the outer cylinder 98. Also, the diameter of the opening end of the case 94 is slightly reduced, which forms a locking portion 118. At the rear end of the outer cylinder 98, a flange portion 120 extending outward is provided. Accordingly, even when the outer cylinder 98 is moved forward, the flange portion 120 is locked by the locking portion 118, so that the outer cylinder 98 can be prevented from coming off. With such configurations, when forward pushing force acts on the shutter 36, the slide arm 96 is moved and elongated. When the pushing force is released, the slide arm 96 is shortened and moved by the biasing force of the spring 110, so as to return to the state as shown in FIG. 6C.

As shown in FIG. 6D, the engaging protrusion 90 is provided on the shutter 36 at a position facing the washing nozzle 30. In the closing state of the shutter 36, the tip of the engaging protrusion 90 is positioned lower than the rotational shaft 88, so that a distance h1 is maintained therebetween in a vertical direction, as shown in FIG. 6D. Accordingly, when the washing nozzle 30 is driven, moment force acts to rotate the shutter 36 clockwise about the rotational shaft 88 in FIG. 6D. Namely, rotating force acts to open the shutter 36 upwardly from the rotational shaft 88.

Also, as shown in FIG. 6E, the engaging protrusion 92 is provided on the shutter 36 at a position facing the washing nozzle 32. In the closing state of the shutter 36, the tip of the engaging protrusion 92 is positioned higher than the rotational shaft 88, so that a distance h2 is maintained therebetween in a vertical direction, as shown in FIG. 6E. Accordingly, when the washing nozzle 32 is driven, moment force acts to rotate the shutter 36 counterclockwise about the rotational shaft 88 in FIG. 6E. Namely, rotating force acts to open the shutter 36 downwardly from the rotational shaft 88.

Figure 7A:
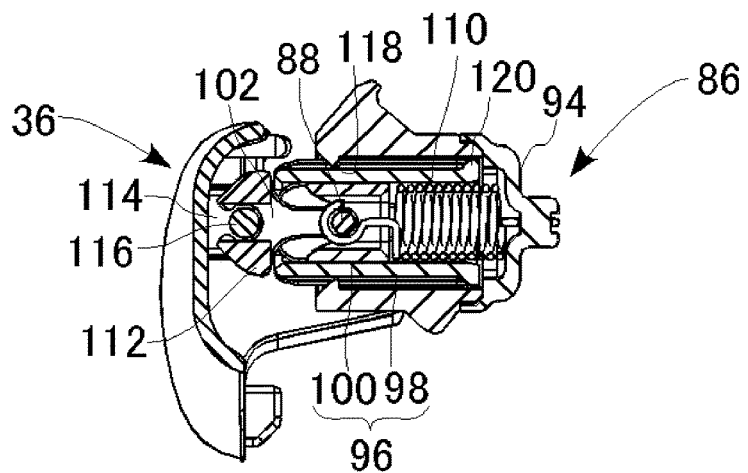
FIGS. 7A-7C are diagrams that show operations of the shutter.
Figure 7B:
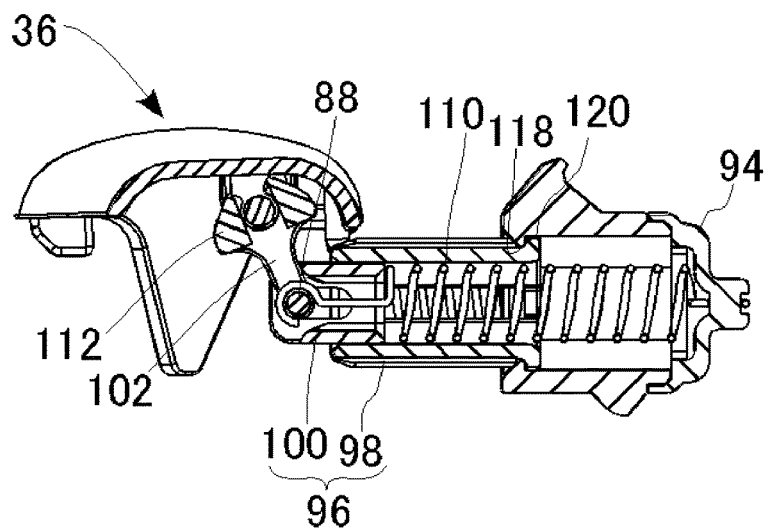
Figure 7C:
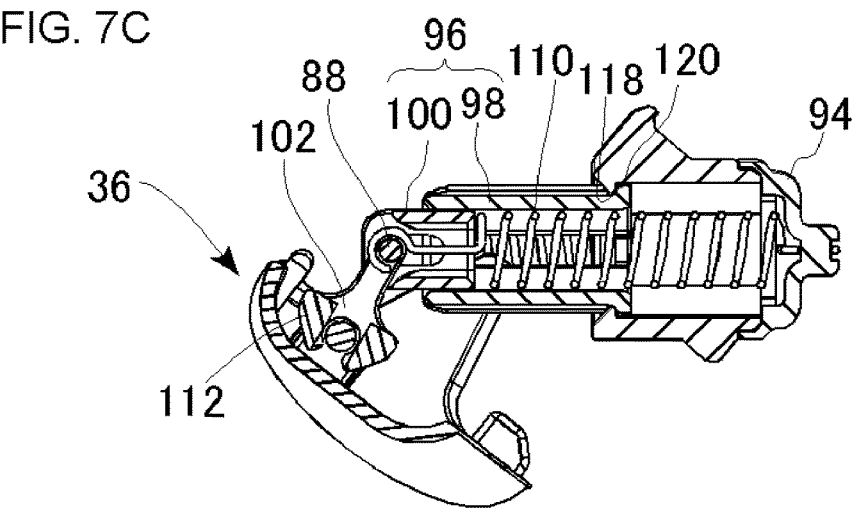

FIGS. 7A-7C are diagrams that show operations of the shutter 36. FIG. 7A is a side view that shows the closing state, FIG. 7B is a sectional view that shows the upward opening state, and FIG. 7C is a sectional view that shows the downward opening state.

In the state where no external force acts on the shutter 36, the spring 110 remains compressed, so that the slide arm 96 also remains shortened, as shown in FIG. 7A. Accordingly, the shutter 36 is drawn by the rotational support mechanisms 86, so as to be placed in the closing state in which the opening 34 is closed.

When the washing nozzle 30 is driven to push the shutter 36 forward in the closing state, the slide arm 96 is elongated against the biasing force of the spring 110, as shown in FIG. 7B. At the time, since a position lower than the rotational shaft 88 on the shutter 36 is pushed, as stated previously, the shutter arm 102 rotates about the rotational shaft 88 to move upward, so that the shutter 36 is placed in the upward opening state.

Also, when the washing nozzle 32 is driven to push the shutter 36 forward in the closing state, the slide arm 96 is elongated against the biasing force of the spring 110, as shown in FIG. 7C. At the time, since a position higher than the rotational shaft 88 on the shutter 36 is pushed, as stated previously, the shutter arm 102 rotates about the rotational shaft 88 to move downward, so that the shutter 36 is placed in the downward opening state.

Next, a method for controlling the private part washing device 4 will be described.

Figure 8A:
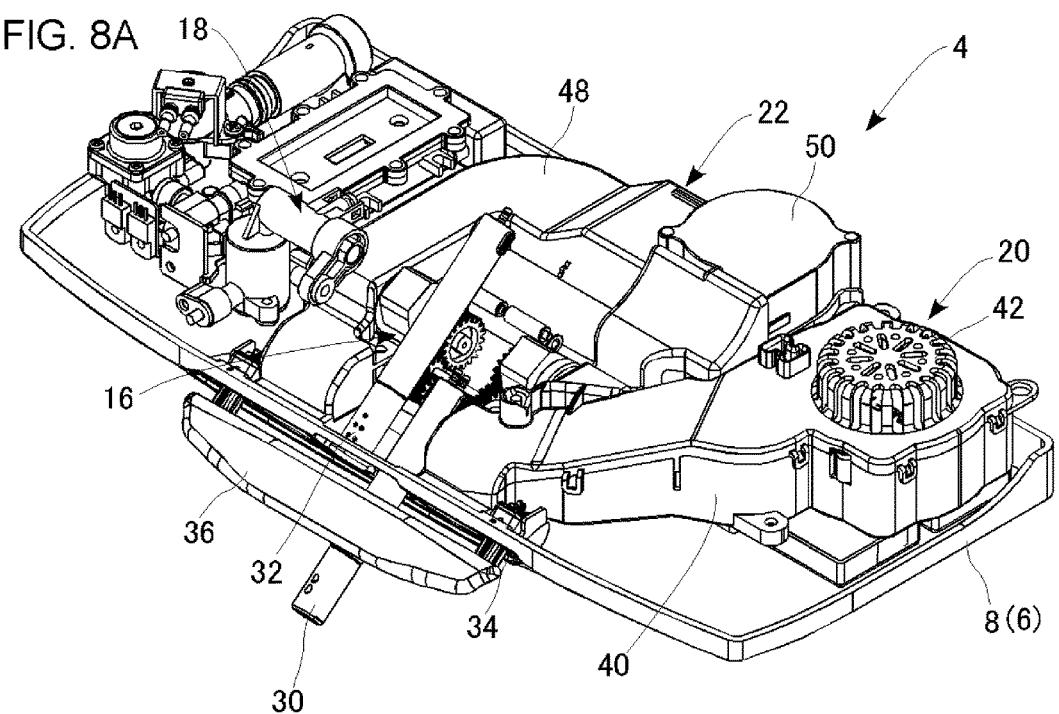
FIGS. 8A-8C are diagrams that show a method for driving and controlling a washing nozzle during anus washing.
Figure 8B:
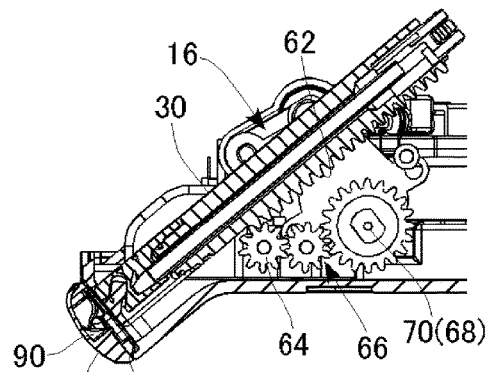
Figure 8C:
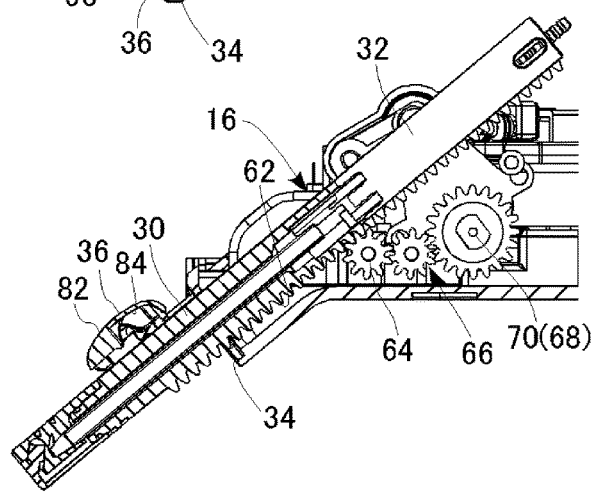
Figure 9A:
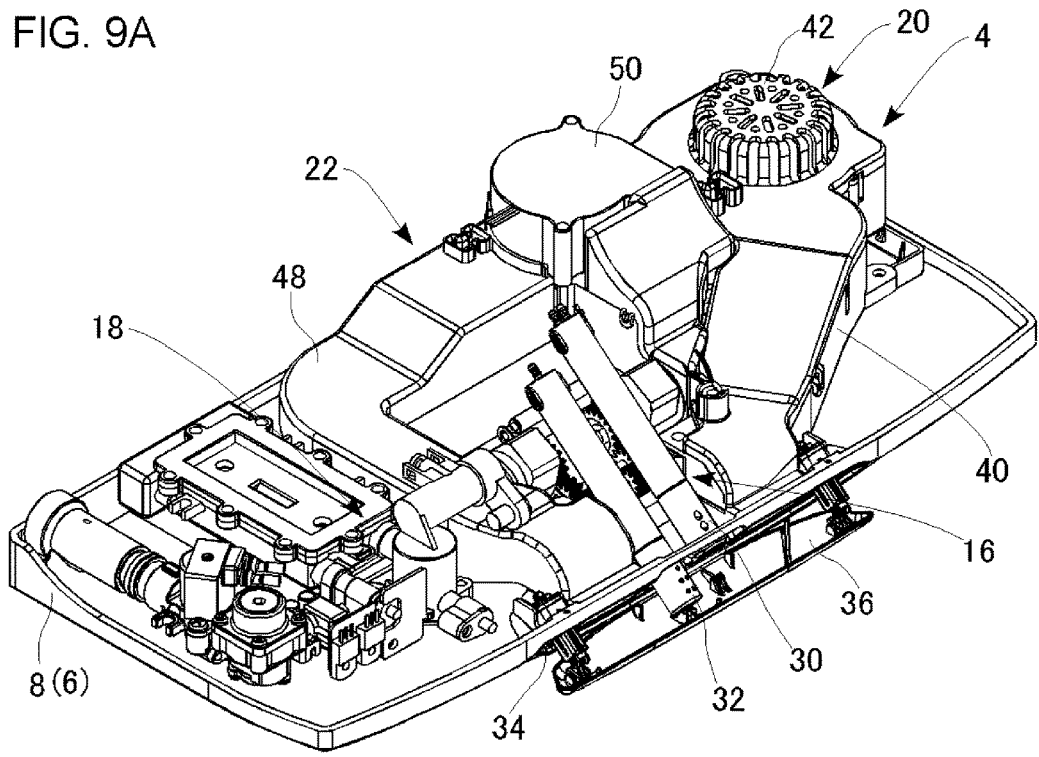
FIGS. 9A-9C are diagrams that show a method for driving and controlling a washing nozzle during warm air drying.
Figure 9B:
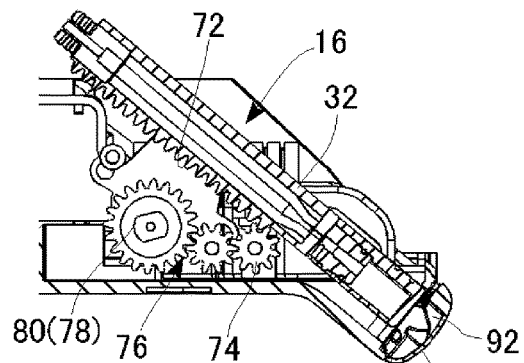
Figure 9C:
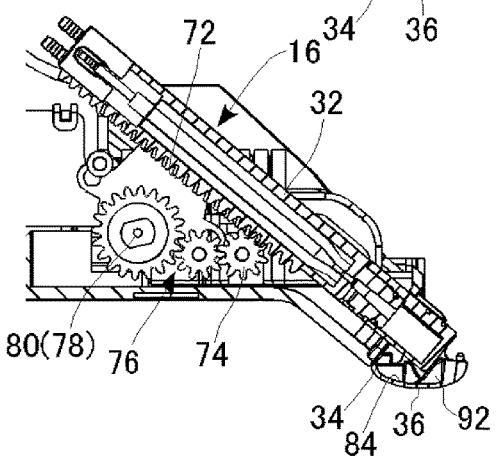
Figure 10A:
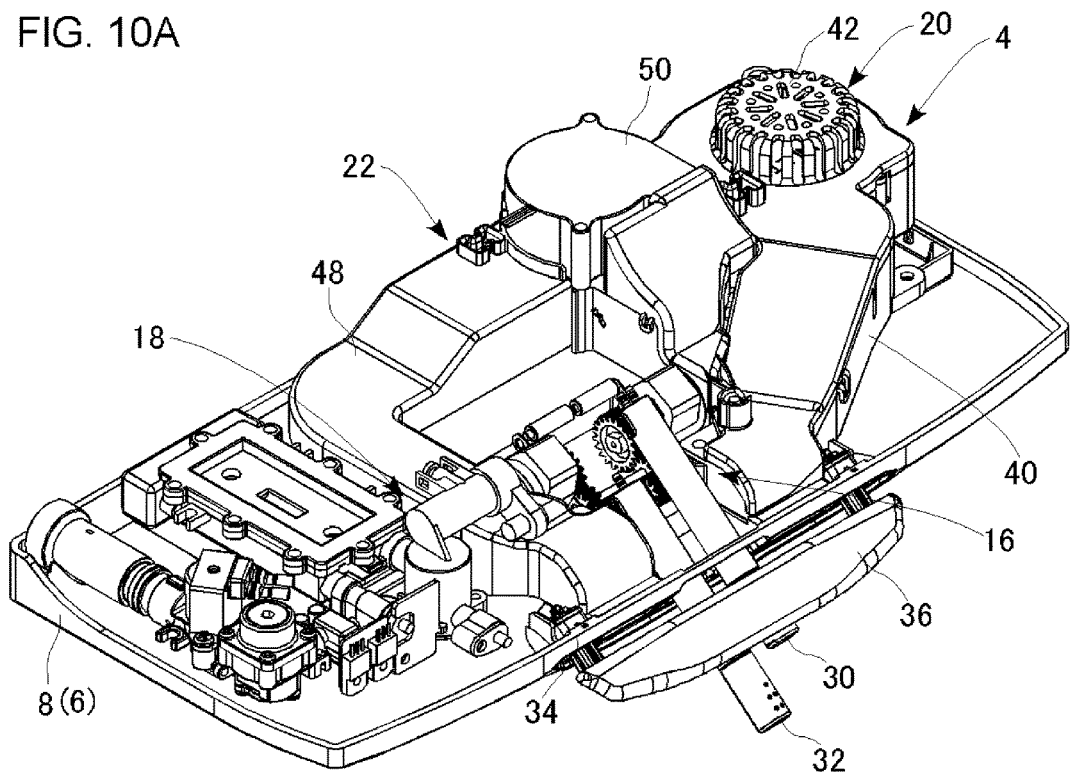
FIGS. 10A-10C are diagrams that show a method for driving and controlling washing nozzles during bidet washing.
Figure 10B:
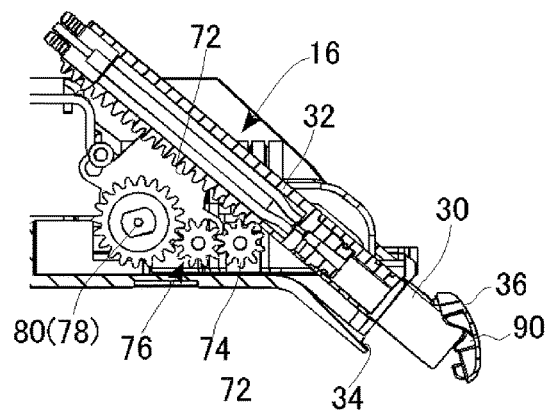
Figure 10C:
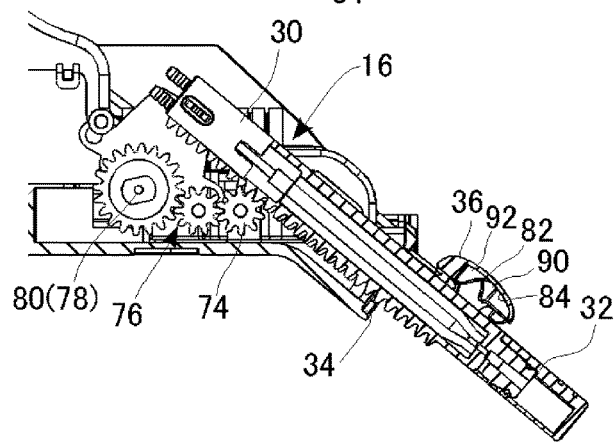

FIGS. 8A-8C are diagrams that show a method for driving and controlling a washing nozzle during anus washing. FIG. 8A is a perspective view that shows an operating state of the washing nozzle. FIGS. 8B and 8C are main sectional views that each show a process of controlling the washing nozzle. FIGS. 9A-9C are diagrams that show a method for driving and controlling a washing nozzle during warm air drying. FIG. 9A is a perspective view that shows an operating state of the washing nozzle. FIGS. 9B and 9C are main sectional views that each show a process of controlling the washing nozzle. FIGS. 10A-10C are diagrams that show a method for driving and controlling washing nozzles during bidet washing. FIG. 10A is a perspective view that shows an operating state of the washing nozzles. FIGS. 10B and 10C are main sectional views that each show a process of controlling the washing nozzles.

As shown in FIGS. 8A-8C, only the washing nozzle 30 is driven in the protruding direction during anus washing. Accordingly, the washing nozzle 30 pushes the engaging protrusion 90, so that the shutter 36 can be placed in the upward opening state. In the upward opening state, since the outer surface 82 of the shutter 36 becomes the upper surface, a splash caused in washing, for example, is unlikely to adhere to the inner surface 84 of the shutter 36. Therefore, when the shutter 36 is closed after the washing, entry of such a splash into the case 6 can be prevented or inhibited.

As shown in FIGS. 9A-9C, only the washing nozzle 32 is driven in the protruding direction during warm air drying. Accordingly, the washing nozzle 32 pushes the engaging protrusion 92, so that the shutter 36 can be placed in the downward opening state. The warm air drying unit 20 is then driven to provide warm air. At the time, the shutter 36 functions as a louver, so that warm air is changed in direction according to the angle of the shutter 36 so as to be delivered to the buttocks of a user. The angle of the shutter 36 can be changed by adjusting the amount of protrusion of the washing nozzle 32. The angle of the shutter 36 may be changed continuously or in stages. Also, the rotating speed of the shutter 36 can be appropriately changed. In the downward opening state, the inner surface 84 of the shutter 36 becomes the upper surface; however, a splash or the like is scarcely caused during warm air drying and is unlikely to adhere to the inner surface 84 of the shutter 36. Therefore, when the shutter 36 is closed after the washing, entry of such a splash into the case 6 can be prevented or inhibited.

As shown in FIGS. 10A-10C, during bidet washing, the washing nozzle 30 is first driven in the protruding direction so as to trigger the upward opening of the shutter 36. The protrusion of the washing nozzle 30 has only to serve as a trigger of the upward opening, and the amount of the protrusion need not be as large as in anus washing. In the present embodiment, the amount of the protrusion is set so that the washing nozzle 30 is hidden by the shutter 36. Thereafter, the washing nozzle 32 is driven in the protruding direction. Accordingly, the washing nozzle 32 protrudes to the washing position, passing under the shutter 36 without pushing the engaging protrusion 92.

In this way, by driving the washing nozzle 30 to start upward opening before driving the washing nozzle 32, the upward opening state can be maintained. Also in the upward opening state thus provided, since the outer surface 82 of the shutter 36 becomes the upper surface, a splash caused in washing, for example, is unlikely to adhere to the inner surface 84 of the shutter 36. Therefore, when the shutter 36 is closed after the washing, entry of such a splash into the case 6 can be prevented or inhibited.

There will now be described a deodorizing method according to the present embodiment.

Figure 11:
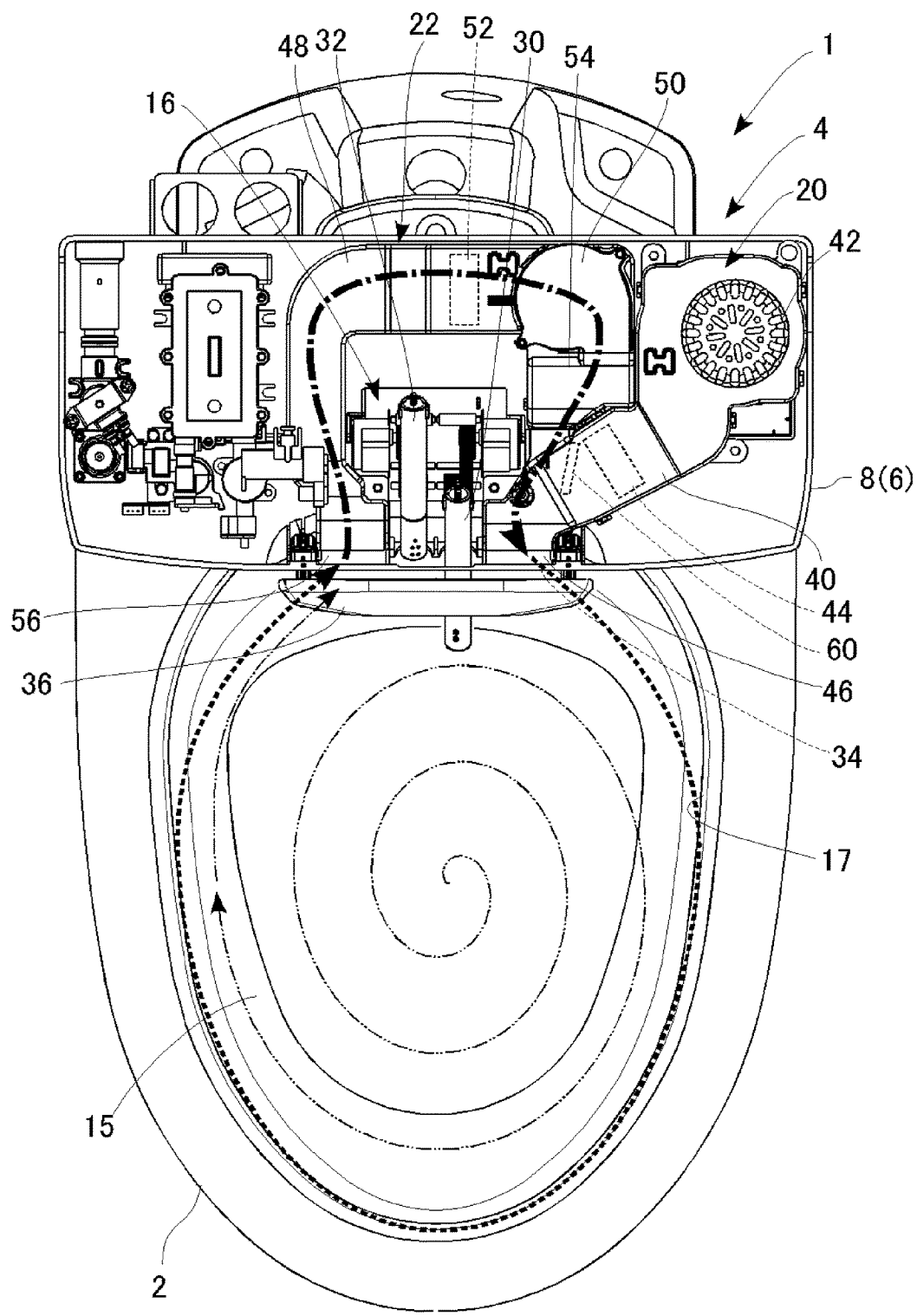
FIG. 11 is a plan view of the toilet that shows a circulation passage for deodorization.
Figure 12:
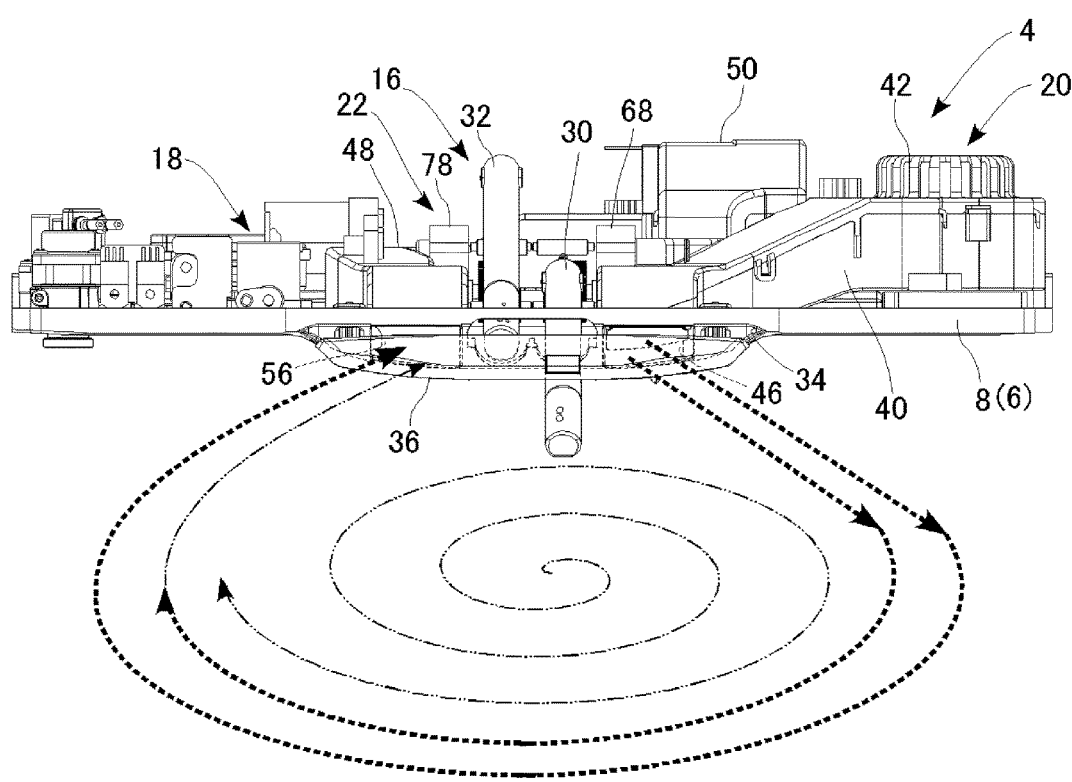
FIG. 12 is a front view of the private part washing device that shows a circulation passage for deodorization.
Figure 13:
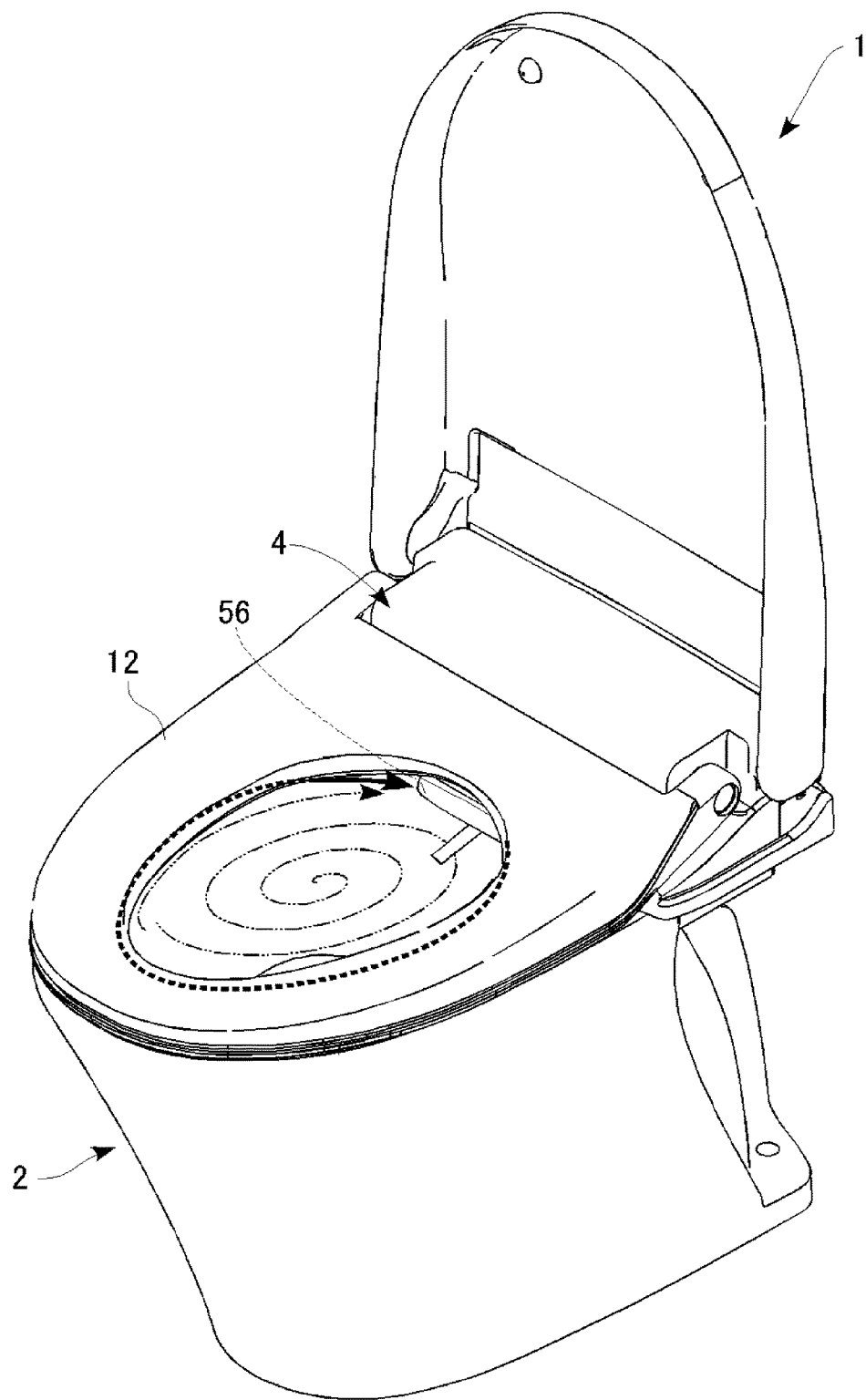
FIG. 13 is a perspective view of the toilet that shows a circulation passage for deodorization.
Figure 14:
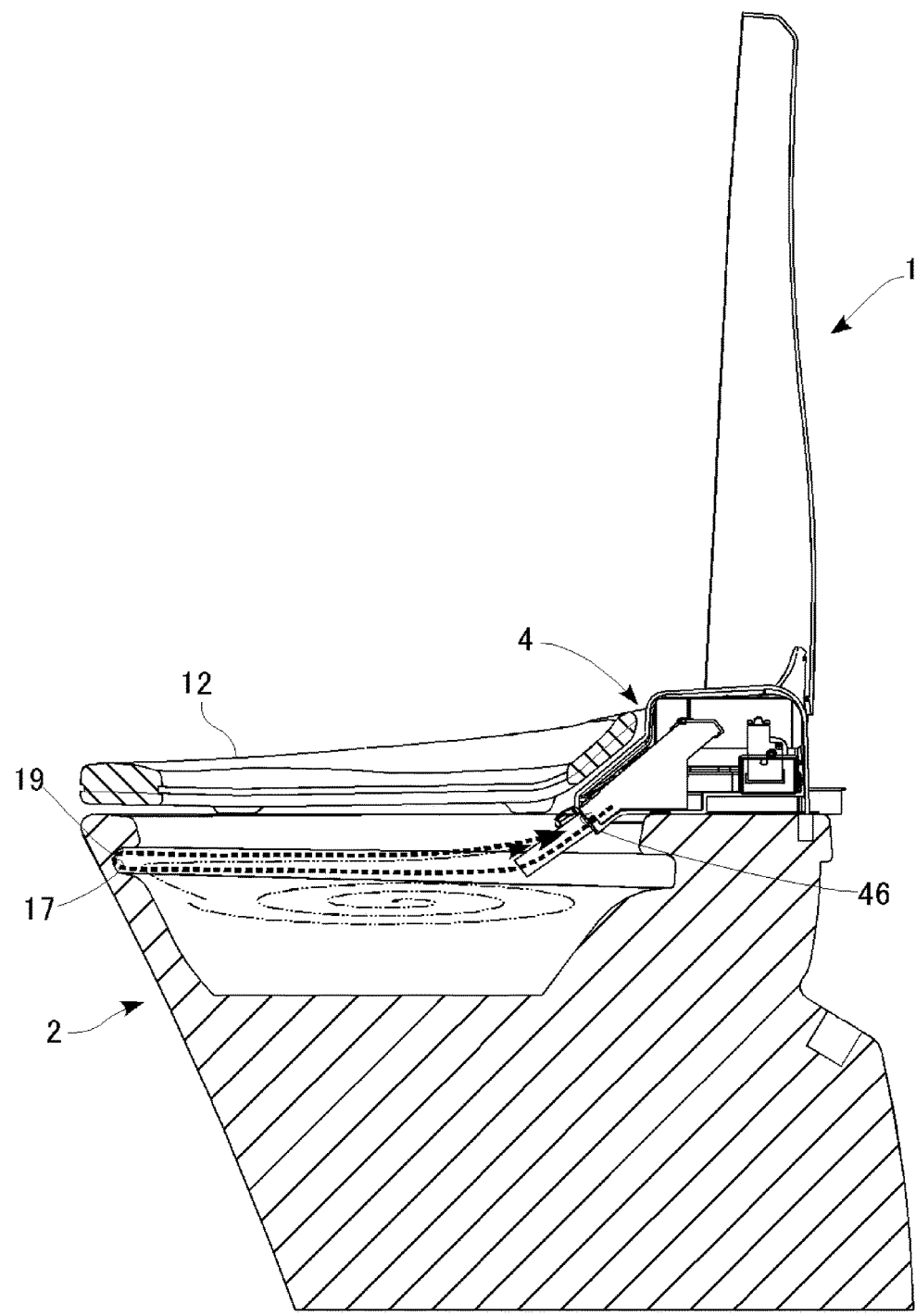
FIG. 14 is a diagram that shows a configuration and an operation of a deodorizing device.

FIGS. 11-14 are diagrams that each show a configuration and an operation of a deodorizing device. FIG. 11 is a plan view of the toilet 1 that shows a circulation passage for deodorization. FIG. 12 is a front view of the private part washing device 4 that shows a circulation passage for deodorization. FIG. 13 is a perspective view of the toilet 1 that shows a circulation passage for deodorization. FIG. 14 is a longitudinal central sectional view of the toilet 1 that shows a circulation passage for deodorization.

In the present embodiment, the private part washing device 4 set forth above is used to efficiently remove odors produced in the toilet main unit 2. As shown in FIGS. 11 and 12, in the private part washing device 4, the expulsion port 46 and suction port 56 of the deodorization duct 48 are arranged side by side on the opening 34 provided on the front of the case 6. As mentioned previously, the expulsion port 46 is also used as the expulsion port of the warm air duct 40.

During deodorization, the washing nozzle 30 is driven so that the shutter 36 is placed in the upward opening state with a predetermined angle, and the fan 50 is driven. The air delivered through the warm air duct 40 is expelled from the expulsion port 46 toward the toilet bowl 15, and the shape and direction of the expulsion port are set so that the air thus blowing off can laterally swirl along the inner surface of the toilet bowl 15, also in consideration of the set angle of the shutter 36.

More specifically, the shape and direction of the expulsion port are set so that the air is expelled toward a rim water passage 17 (see FIG. 14) provided in the upper portion of the toilet bowl 15. The rim water passage 17 is a "rim-like pathway" of a groove shape provided along the inner surface of the toilet bowl 15 so as to circle the toilet bowl 15, of which the intended function is to generate a swirling flow of flush water (water used to flush the toilet bowl 15). In the present embodiment, the rim water passage 17 also functions to generate a swirling flow of air during deodorization in which flush water is not provided. Accordingly, air blowing off from the expulsion port 46 for deodorization laterally swirls along the rim water passage 17 within the toilet bowl 15 and returns to the private part washing device 4 side. Namely, a swirl passage as indicated by a dotted arrow in the figures is formed within the toilet bowl 15.

Meanwhile, the shape and direction of the suction port 56 are set so that the suction port 56 opens toward the passage of air that has swirled within the toilet bowl 15 and returned as described above. Accordingly, the air that has flowed along the swirl passage is naturally led to the suction port 56 to be delivered into the deodorization duct 48. The fan 50 is driven during deodorization, and a deodorization passage as indicated by a dashed dotted arrow in FIG. 11 is formed within the deodorization duct 48. Namely, a circulation passage for repeatedly circulating air is formed by the swirl passage of air within the toilet bowl 15 and the deodorization passage within the deodorization duct 48.

As shown in FIG. 14, the rim water passage 17 has an upper wall 19 that overhangs the airflow in the rim water passage 17. Also, as shown in FIG. 13, the toilet seat 12 provided upon the toilet main unit 2 overhangs the upper opening of the toilet main unit 2. Accordingly, upward leakage of laterally swirling air from the toilet main unit 2 can be effectively prevented.

With the configuration stated above, the fan 50 is driven during deodorization, and air is expelled from the expulsion port 46, laterally swirls along the rim water passage 17, and then returns. At the time, the lateral swirl generates a flow (swirling flow) of air within the toilet bowl 15, as indicated by a dashed double-dotted line in the figures, so that stale air can also be taken into the suction port 56. The air taken into the suction port 56 is deodorized by the deodorizing cartridge 52, bacteria in the air are removed by the bacteria removal unit 54, and the air is expelled again from the expulsion port 46. Once such a circulation flow of air is formed, the air flows under its own inertia thereafter, so that the deodorization can be efficiently continued without the need to increase the output of the fan 50. In this way, by repeatedly circulating and deodorizing odorous air, the deodorization effect can be improved. Especially, since the air is made to laterally swirl along the rim water passage 17 within the toilet bowl 15, rise of odor from the toilet main unit 2 can be effectively prevented.

A preferable embodiment of the present invention has been described. However, the present invention is not limited to the specific embodiment, and it will be obvious that various modifications could be developed within the scope of the technical idea of the present invention.

Although not mentioned in the embodiment, in order to optimize the lateral swirl of air within the toilet bowl 15, the angle of the shutter 36 or the air volume from the shutter 36 may be appropriately adjusted. For example, electronic control may be performed in which the volume of air blowing off from the deodorizing unit 22 or the volume of air returning to the deodorizing unit 22 is detected, and the angle of the shutter 36 or the air volume from the shutter 36 is appropriately changed according to the detection result.

Although not mentioned in the embodiment, a guide rib, which is movable in the horizontal directions (lateral directions) and used to adjust air direction, may be provided on the shutter so as to appropriately switch the air direction during deodorization and warm air drying. By providing such a guide rib, the air blowing off from the expulsion port 46 can be accurately led to the rim water passage 17.

Although not mentioned in the embodiment, the fan 42 for warm air may be driven during deodorization so as to assist the fan 50. In this case, since the air provided by the fan 42 need not be warm air, the fan 42 may be driven while the heater 44 is turned off. The air volume from the fan 50 and that from the fan 42 can be adjusted based on the position of the damper 60. Namely, the ratio between the opening of the deodorization passage and the opening of the warm airflow passage can be changed based on the position of the damper 60.

In the embodiment described above, the expulsion port 46 and the suction port 56 of the deodorizing device are provided at the same height position, as shown in FIG. 12. In a modification, the expulsion port 46 may be arranged lower than the suction port 56 so that stale air in the lower part of the toilet bowl 15 can be actively swirled and circulated. In this case, circulating air is laterally swirled and also led upward, and, along the rim-like pathway of the rim water passage 17 or the rim-like pathway formed under the toilet seat 12, the air is led to the suction port 56.

Although not mentioned in the embodiment, an air direction guide rib for directing an airflow may be provided on the inner side of the toilet seat 12, so that the circulation passage may be formed using the air direction guide rib.

Although not mentioned in the embodiment, the fan 42 may also have the functions of the fan 50. More specifically, the deodorization duct 48 may be connected to the upstream side of the warm air duct 40 so that the fan 42 can be used to send air in the deodorization passage. Accordingly, the fan 50 and damper 60 can be omitted, so that the necessary parts can be reduced. In this case, the deodorizing cartridge 52 and the bacteria removal unit 54 are preferably provided on the upstream side of the fan 42. The heater 44 may be turned on only during warm air drying.

Although not mentioned in the embodiment, the damper 60 may be a mechanical damper of which the angle is autonomously switched according to the air direction or strength of the airflow, or may be a damper of which the angle is electrically adjustable by means of a motor or the like.

The present invention is not limited to the embodiment or modifications stated above and may also be implemented by modifying the constituting elements without departing from the scope of the invention. Various inventions may be developed by appropriately combining the constituting elements disclosed in the embodiment or modifications stated above. Also, some of the constituting elements disclosed in the embodiment or modifications may be omitted.

One embodiment of the present invention is a deodorizing method for removing odors within a flush-toilet toilet bowl. The deodorizing method comprises: providing, in a rear portion of a toilet main unit, a deodorizing device having an air expulsion port and an air suctioning port; circulating air by expelling air through the expulsion port such as to laterally swirl the air along an inner surface of the toilet bowl, and suctioning swirled returning air via the suctioning port; and carrying out deodorization in the course of circulating the air.

According to this embodiment, air is expelled from the deodorizing device provided in a rear portion of the toilet main unit, laterally swirls along the inner surface of the toilet bowl, and then returns. The lateral swirl generates a flow of air within the toilet bowl, so that stale air can also be taken into the suction port. The air taken into the suction port is deodorized within the deodorizing device and then is expelled again from the expulsion port. Thus, there is formed a circulation passage that connects a swirl passage along the inner surface of the toilet bowl and a deodorization passage within the deodorizing device. Once such a circulation flow of air is formed, the air flows under its own inertia thereafter, so that the deodorization can be efficiently continued without the need to increase the output of the fan. Especially, since the air is made to laterally swirl within the toilet bowl, rise of odor from the toilet main unit can be effectively prevented.

Another embodiment of the present invention is a deodorizing device. The deodorizing device for removing odors within a flush-toilet toilet bowl, comprises: a deodorization passage, provided in a rear portion of a toilet main unit, having at one end thereof an air expulsion port, having at another end thereof an air suctioning port, and furnished midway thereof with a deodorizing section; and a blower enabled for generating a flow of air in the deodorization passage; wherein the expulsion port is arranged so as to open in a direction enabling air expelled therefrom to swirl laterally along an inner surface of the toilet bowl, and the suctioning port is arranged so as to open on a flow pathway of air returning from swirling along the toilet bowl.

According to this embodiment, air is expelled from the expulsion port, laterally swirls along the inner surface of the toilet bowl, and then returns. The lateral swirl generates a flow of air within the toilet bowl, so that stale air can also be taken into the suction port. The air taken into the suction port is deodorized by the deodorizing section and then is expelled again from the expulsion port. Thus, there is formed a circulation passage that connects a swirl passage along the inner surface of the toilet bowl and the deodorization passage within the deodorizing device. Once such a circulation flow of air is formed, the air flows under its own inertia thereafter, so that the deodorization can be efficiently continued without the need to increase the output of the fan. Especially, since the air is made to laterally swirl within the toilet bowl, rise of odor from the toilet main unit can be effectively prevented.

Yet another embodiment of the present invention is a flush toilet. The flush toilet is furnished with a deodorizing device for removing odors within a main unit of the toilet, and the deodorizing device comprises: a deodorization passage, provided in a rear portion of the toilet main unit, having at one end thereof an air expulsion port, having at another end thereof an air suctioning port, and furnished midway thereof with a deodorizing section; and a blower enabled for generating a flow of air in the deodorization passage; wherein the expulsion port is arranged so as to open in a direction enabling air expelled therefrom to swirl laterally along an inner surface of a bowl of the toilet, and the suctioning port is arranged so as to open on a flow pathway of air returning from swirling along the toilet bowl, the flush toilet is configured to enable an air-swirling passage within the toilet bowl, and said deodorization passage to form a circulation passage for circulating air, and the swirling passage is configured by a rim-like pathway formed in an upper portion of the toilet main unit.

According to this embodiment, air is expelled from the expulsion port of the deodorization passage, laterally swirls along the rim-like pathway formed in an upper portion of the toilet main unit, and then returns. Namely, the swirl passage is formed utilizing the original shape of the toilet main unit. The lateral swirl generates a flow of air within the toilet bowl, so that stale air can also be taken into the suction port. The air taken into the suction port is deodorized by the deodorizing section and then is expelled again from the expulsion port. Thus, there is formed a circulation passage that connects the swirl passage along the inner surface of the toilet bowl and the deodorization passage within the deodorizing device. Once such a circulation flow of air is formed, the air flows under its own inertia thereafter, so that the deodorization can be efficiently continued without the need to increase the output of the fan. Especially, since the air is made to laterally swirl within the toilet bowl, rise of odor from the toilet main unit can be effectively prevented.

The rim-like pathway may have an upper wall positioned above the swirling passage. According to this embodiment, a rim structure formed in an upper portion of the toilet main unit overhangs the swirling flow, so that upward leakage of odorous air from the toilet main unit can be effectively prevented.

The flush toilet may further comprise: a case provided on an upper side of a rear portion of a toilet main unit, and having an opening on its front side; a warm airflow passage housed in the case; and a warm airflow generator housed in the case and enabled for generating a warm airflow current in the warm airflow passage, wherein: the deodorization passage is housed in the case; the deodorization passage and the warm airflow passage have a shared passage; and the expulsion port for the deodorization passage serves dually as an expulsion port for the warm airflow passage.

According to this embodiment, a part of the deodorizing device is shared by a warm air device used for warm air drying after pubic lavage, thereby saving space in the flush toilet as a whole. If a fan is also shared by the deodorizing device and warm air device, necessary parts can also be reduced. Conversely, by providing a fan in each of the deodorizing device and warm air device and appropriately driving the fan in the warm air device when the deodorizing device is driven, the air blowing capacity can be improved.

In this case, a damper may be provided upstream of the shared passage, for switching between opening states of the deodorization passage and the warm airflow passage. In the switching of the opening states, one of the deodorization passage and the warm airflow passage may be blocked when the other is opened. Alternatively, blocking of only one of either the deodorization passage or the warm airflow passage may be enabled, and the ratio between the opening of the deodorization passage and the opening of the warm airflow passage may be changed based on the position of the damper. For example, if blocking of the deodorizing device side is only enabled, mixing of deodorized air with warm air can be prevented during warm air drying, and, in addition, the strength of the airflow can be increased using warm air during deodorization.

What is claimed is:

1. A deodorizing method for removing odors within a flush-toilet toilet bowl, the deodorizing method comprising: providing, in a rear portion of a toilet main unit, a deodorizing device having an air expulsion port and an air suctioning port; circulating air by expelling air through the expulsion port toward a lateral inner surface of the toilet bowl to laterally swirl the air along an inner surface of the toilet bowl, and suctioning swirled returning aft via the suctioning port; and carrying out deodorization in the course of circulating the air.

2. A deodorizing device for removing odors within a flush-toilet toilet bowl, the deodorizing device comprising:
   a deodorization passage, provided in a rear portion of a toilet main unit, having at one end thereof an air expulsion port, having at another end thereof an air suctioning port, and furnished midway thereof with a deodorizing section; and
   a blower enabled for generating a flow of air in the deodorization passage;
   wherein the expulsion port is arranged so as to open toward a lateral inner surface of the toilet bowl to enable air expelled therefrom to swirl laterally along an inner surface of the toilet bowl, and the suctioning port is arranged so as to open on a flow pathway of air returning from swirling along the toilet bowl.

3. A flush toilet furnished with a deodorizing device for removing odors within a main unit of the toilet, the deodorizing device comprising:
   a deodorization passage, provided in a rear portion of a toilet main unit, having at one end thereof an air expulsion port, having at another end thereof an air suctioning port, and furnished midway thereof with a deodorizing section; and
   a blower enabled for generating a flow of air in the deodorization passage;
   wherein the expulsion port is arranged so as to open toward a lateral inner surface of the toilet bowl to enable air expelled therefrom to swirl laterally along an inner surface of a bowl of the toilet, and the suctioning port is arranged so as to open on a flow pathway of air returning from swirling along the toilet bowl,
   wherein the flush toilet is configured to enable an air-swirling passage within the toilet bowl, and said deodorization passage to form a circulation passage for circulating air, and
   wherein the swirling passage is configured by a rim-like pathway formed in an upper portion of the toilet main unit.

4. The flush toilet of claim 3, wherein the rim-like pathway has an upper wall positioned above the swirling passage.

5. The flush toilet of claim 3, further comprising:
   a case provided on an upper side of a rear portion of the toilet main unit, and having an opening on its front side;
   a warm airflow passage housed in the case; and
   a warm airflow generator housed in the case and enabled for generating a warm airflow current in the warm airflow passage;
   wherein the deodorization passage is housed in the case,
   wherein the deodorization passage and the warm airflow passage have a shared passage, and
   wherein the expulsion port for the deodorization passage serves dually as an expulsion port for the warm airflow passage.

6. The flush toilet of claim 5, comprising a damper provided upstream of the shared passage, for switching between opening states of the deodorization passage and the warm airflow passage.

7. A deodorizing method for removing odors within a flush-toilet toilet bowl, the deodorizing method comprising: providing, in a rear portion of a toilet main unit, a deodorizing device having an air expulsion port and an air suctioning port; generating a flow of air so as expel the air through the expulsion port toward a lateral inner surface of the toilet bowl such as to laterally swirl the air along an inner surface of the toilet bowl, and to suction swirled returning air via the suctioning port; and carrying out deodorization in the course of generating the flow of air.

* * * * *